United States Patent
Purvis, Jr.

(10) Patent No.: US 8,187,885 B2
(45) Date of Patent: May 29, 2012

(54) MICROBEAD KIT AND METHOD FOR QUANTITATIVE CALIBRATION AND PERFORMANCE MONITORING OF A FLUORESCENCE INSTRUMENT

(75) Inventor: Norman Baylis Purvis, Jr., Franklin, TN (US)

(73) Assignee: Nodality, Inc., South San Francisco, CA (US)

( * ) Notice: Subject to any disclaimer, the term of this patent is extended or adjusted under 35 U.S.C. 154(b) by 147 days.

(21) Appl. No.: 12/776,349

(22) Filed: May 7, 2010

(65) Prior Publication Data

US 2010/0285594 A1    Nov. 11, 2010

Related U.S. Application Data

(60) Provisional application No. 61/176,420, filed on May 7, 2009.

(51) Int. Cl.
*G01N 31/00* (2006.01)
*G01N 21/64* (2006.01)

(52) U.S. Cl. ......... 436/8; 436/164; 436/172; 422/82.05; 422/82.08; 422/430; 435/810; 73/1.01; 73/1.02; 73/1.03

(58) Field of Classification Search ............... 436/8, 10, 436/63, 164, 172, 808; 422/82.05, 82.08, 422/430; 435/810; 73/1.01, 1.02, 1.03
See application file for complete search history.

(56) References Cited

U.S. PATENT DOCUMENTS

| | | | |
|---|---|---|---|
| 4,157,323 A | 6/1979 | Yen et al. | |
| 4,285,819 A | 8/1981 | Yen et al. | |
| 4,326,008 A | 4/1982 | Rembaum | |
| 4,357,668 A | 11/1982 | Schwartz et al. | |
| 4,609,689 A | 9/1986 | Schwartz et al. | |
| 4,699,826 A * | 10/1987 | Schwartz et al. | 428/402 |
| 4,699,828 A | 10/1987 | Schwartz et al. | |
| 4,704,891 A | 11/1987 | Recktenwald et al. | |
| 4,714,682 A | 12/1987 | Schwartz | |
| 4,767,206 A | 8/1988 | Schwartz | |
| 4,774,189 A * | 9/1988 | Schwartz | 436/10 |
| 4,816,567 A | 3/1989 | Cabilly et al. | |
| 4,828,984 A | 5/1989 | Schwartz | |
| 4,857,451 A | 8/1989 | Schwartz | |
| 4,868,126 A | 9/1989 | Schwartz | |
| 4,918,004 A | 4/1990 | Schwartz | |
| 5,073,497 A | 12/1991 | Schwartz | |
| 5,073,498 A | 12/1991 | Schwartz et al. | |
| 5,084,394 A | 1/1992 | Vogt et al. | |
| 5,089,416 A | 2/1992 | Schwartz et al. | |
| 5,093,234 A | 3/1992 | Schwartz | |
| 5,144,224 A | 9/1992 | Larsen | |
| 5,314,824 A | 5/1994 | Schwartz | |
| 5,380,663 A | 1/1995 | Schwartz et al. | |
| 5,540,494 A | 7/1996 | Purvis et al. | |
| 5,620,842 A | 4/1997 | Davis et al. | |
| 5,644,048 A | 7/1997 | Yau | |
| 5,747,349 A * | 5/1998 | van den Engh et al. | 436/172 |
| 5,837,547 A | 11/1998 | Schwartz | |
| 5,968,738 A | 10/1999 | Anderson et al. | |
| 6,074,879 A | 6/2000 | Zelmanovic et al. | |
| 6,495,333 B1 | 12/2002 | Willmann et al. | |
| 6,521,729 B1 | 2/2003 | Zelmanovic et al. | |
| 6,542,833 B1 | 4/2003 | Nygaard | |
| 6,897,954 B2 | 5/2005 | Bishop et al. | |
| 6,906,792 B2 | 6/2005 | Ortyn et al. | |
| 6,951,727 B2 | 10/2005 | Davis | |
| 7,381,535 B2 | 6/2008 | Perez et al. | |
| 7,393,656 B2 | 7/2008 | Perez et al. | |
| 7,563,584 B2 | 7/2009 | Perez et al. | |
| 7,695,924 B2 | 4/2010 | Perez et al. | |
| 7,695,926 B2 | 4/2010 | Perez et al. | |
| 2005/0175979 A1 | 8/2005 | Williams | |
| 2006/0131361 A1 | 6/2006 | Eastman et al. | |
| 2007/0009923 A1 | 1/2007 | Nolan et al. | |
| 2007/0196869 A1 | 8/2007 | Perez et al. | |
| 2009/0081699 A1 | 3/2009 | Perez et al. | |
| 2009/0098594 A1 | 4/2009 | Fantl et al. | |
| 2009/0291458 A1 | 11/2009 | Cohen et al. | |
| 2010/0086951 A1 | 4/2010 | Hedley et al. | |
| 2010/0240542 A1 | 9/2010 | Soper et al. | |

FOREIGN PATENT DOCUMENTS

| | | |
|---|---|---|
| EP | 0511314 B1 | 12/1996 |
| WO | WO 94/24314 A1 | 10/1994 |
| WO | WO 03/067210 A2 | 8/2003 |
| WO | WO 03/067210 A3 | 12/2003 |
| WO | WO 2009/025847 A2 | 2/2009 |
| WO | WO 2009/025847 A3 | 6/2009 |
| WO | WO 2010/006291 A1 | 1/2010 |
| WO | WO 2010/028277 A1 | 3/2010 |
| WO | WO 2010/045651 A1 | 4/2010 |
| WO | WO 2010/135608 A1 | 11/2010 |

OTHER PUBLICATIONS

U.S. Appl. No. 61/048,657, filed May 4, 2009, Covey et al.
U.S. Appl. No. 61/048,886, filed Apr. 29, 2008, Fantl et al.
U.S. Appl. No. 61/048,920, filed Apr. 29, 2008, Fantl et al.
U.S. Appl. No. 61/079,537, filed Jul. 10, 2008, Putta.
U.S. Appl. No. 61/079,579, filed Jul. 10, 2008, Banville et al.
U.S. Appl. No. 61/120,320, filed Dec. 5, 2008, Fantl et al.
Beaucage, et al. The Functionalization of Oligonucleotides via Phosphoramidite Derivatives. Tetrahedron. 49 1993. 10:1925.
Brill, et al. Synthesis of Oligodeoxynucleoside Phophorpdithioates vi Thioamidites. J. Am. Chem. Soc. 1989. 111:2321-2322.
Carlsson, et al. Screening for genetic mutations. Nature 1996. 380:207.
Chalfie, et al. Green fluorescent protein as a marker for gene expression. Science 1994. 263(5148):802-805.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

(Continued)

*Primary Examiner* — Maureen Wallenhorst
(74) *Attorney, Agent, or Firm* — Wilson Sonsini Goodrich & Rosati

(57) ABSTRACT

Fluorescently labeled microsphere calibration and quality control particles for use in establishing standardized fluorescence detector setup, monitoring daily QC of flow cytometers and quantitative calibration of the fluorescence detectors in traceable units of measure (molecules equivalent soluble fluorescence; MESF).

21 Claims, 2 Drawing Sheets

OTHER PUBLICATIONS

Clark, et al. Antibody humanization: a case of the 'Emperor's new clothes'? Immunol. Today 2000. 21(8):397-402.

Crans-Vargas, et al. CREB as a prognostic marker in acute leukemia. Abstract. Blood. 2001; 98(11), part 1, p. 316a.

Duncan, et al. A new reagent which may be used to introduce sulfhydryl groups into proteins, and its use in the preparation of conjugates for immunoassay. Anal Biochem. Jul. 1, 1983;132(1):68-73.

Egholm, et al. Peptide Nucleic Acids (PNA). Oligonucleotide Analogues with an Achiral Peptide Backbone. J. Am. Chem. Soc. (1992). 114:1895-1897.

Egholm, et al. PNA hybridizes to complementary oligonucleotides obeying the Watson-Crick hydrogen-bonding rules. Nature. Oct. 7, 1993;365(6446):566-8.

European search report and search opinion dated Feb. 22, 2011 for Application No. 10180167.8.

Heim, et al. Engineering green fluorescent protein for improved brightness, longer wavelengths and fluorescence resonance energy transfer. Curr Biol. 1996. 6(2):178-82.

Irish, et al. Single cell profiling of potentiated phospho-protein networks in cancer cells. Cell. Jul. 23, 2004;118(2):217-28.

Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.

Kitts. Cloning vector pEGFP-N1, complete sequence, enhanced green fluorescent protein (egfp) and neomycin phosphotransferase genes, complete cds. Clontech—Genbank Accession No. U55762. 1996. Genbank.

Kolb et al., Electrochemical Surface Science. Angewandte Chemie International Edition 2001. 40:1162-1181.

Kornblau, et al. Dynamic single-cell network profiles in acute myelogenous leukemia are associated with patient response to standard induction therapy. Clin Cancer Res. Jul. 15, 2010;16(14):3721-33. (abstract).

Krutzik et al. Intracellular phospho-protein staining techniques for flow cytometry: monitoring single cell signaling events. Cytometry A 2003. 55:61-70.

Krutzik, et al. Analysis of protein phosphorylation and cellular signaling events by flow cytometry: techniques and clinical applications. Clinical Immunology. 2004; 110:206-21.

Letsinger, et al. Cationic Oligonucleotides. J. Am. Chem. Soc. 1988. 110:4470.

Letsinger, et al. Effects of pendant groups at phosphorus on binding properties of d-ApA analogues. Nucl. Acids Res. 1986. 14(8):3487-3499.

Letsinger, et al. Phosphoramidate Analogs of Oligonucleotides. J. Org. Chem. 1970. 35(11): 3800-3803.

Mag, et al. Synthesis and selective cleavage of an oligodeoxynucleotide containing a bridged internucleotide 5'-phosphorothioate linkage. Nucleic Acids Res. 1991. 19(7):1437-1441.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Meier, et al. Peptide Nucleic Acids (PNAs)—Unusual Properties of Nonionic Oligonucleotide Analogues. Angew. Chem. Int. Ed. Engl. 1992. 31(8):1008-1010.

Nolan, et al. Fluorescence-activated cell analysis and sorting of viable mammalian cells based on β-D-galactosidase activity after transduction of *Escherichia coli lacZ*. Proc Natl Acad Sci USA 1988. 85: 2603-2607.

Paywels, et al. Biological Activity of New 2-5 A Analogues. Chemica Scripta 1986 26:141-9.

Perez, et al. LFA-1 signaling through p44/42 is coupled to perforin degranulation in CD56+CD8+ natural killer cells. Blood. Aug. 15, 2004;104(4):1083-93.

Perez, et al. Simultaneous measurement of multiple active kinase states using polychromatic flow cytometry. Nat Biotechnol. 2002. 20: 155-62.

Perfetto, et al. Seventeen-colour flow cytometry: unravelling the immune system. Nat Rev Immunol. 2004. 4:648-655.

Purvis, et al. Multi-platform, multi-site instrumentation and reagent standardization. Cytometry 1998. 33: 156-165.

Rosen, et al. Functional characterization of FLT3 receptor signaling deregulation in acute myeloid leukemia by single cell network profiling (SCNP). PLoS One. Oct. 27, 2010;5(10):e13543.

Sawai, et al. Synthesis and properties of oligoadenylic acids containing 2'-5' phosphoramide linkage. Chem. Lett. 1984; 805-808.

Schwartz, et al. Quantitating Fluorescence Intensity from Fluorophore: The Definition of MESF Assignment. J. Res. Natl. Inst. Stand. Technol. 2002. 107: 83-91.

Schwartz, et al. Standardizing flow cytometry: a classification system of fluorescence standards used for flow cytometry. Cytometry 1998. 33: 106-114.

Schwartz, et al. Standardizing flow cytometry: construction of a standardized fluorescence calibration plot using matching spectral calibrators. Cytometry 1996. 26: 22-31.

Schwartz, et al. Formalization of the MESF unit of fluorescence intensity. Cytometry Part B Clinical Cytometry. 2004. 57B:1-6.

Shaner, et al. A guide to choosing flourescent proteins. Nature Methods. 2005. 2(12):905-909.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005;7(4):351-62.

Spiekermann, et al. Overexpression and constitutive activation of FLT3 induces STAT5 activation in primary acute myeloid leukemia blast cells. Clinical Cancer Research. Jun. 2003; 9:2140-2150.

Sprinzl, et al. Enzymatic Incorporation of ATP and CTP Analogues into the 3' End of tRNA. Eur. J. Biochem. 1977. 81:579-589.

Stauber, et al. Development and Applications of Enhanced Green Fluorescent Protein Mutants. BioTechniques. 1998. 24(3):462-471.

UK office action and search report dated Feb. 22, 2011 for GB Application No. 1017857.2.

Vanhest, et al. Efficient Introduction of Alkene Functionality into Prteins in vivo. FEBS Lett. 1998. 428: 68-70.

Wang, et al. Quantitating Fluorescence Intensity From Fluorophores: Practical Use of MESF Values, J. Res. Natl. Inst. Stand. Technol. 107, 339-353 (2002).

Wang, et al. Recent advances in the chemistry of lanthanide-doped upconversion nanocrystals. Chem Soc Rev. Apr. 2009;38(4):976-89.

Wang, et al. Toward Quantitative Fluorescence Measurements with Multicolor Flow Cytometry, Cytometry Part A, 73A: 279-288, 2008.

Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.

\* cited by examiner

MICROBEAD KIT AND METHOD FOR QUANTITATIVE CALIBRATION AND PERFORMANCE MONITORING OF A FLUORESCENCE INSTRUMENT

CROSS-REFERENCE

This application claims the benefit of U.S. Provisional Application No. 61/176,420, filed May 7, 2009, which application is incorporated herein by reference.

BACKGROUND OF THE INVENTION

Fluorescence-based assays are widely used in scientific research and clinical pathology. Generally, fluorescence-based assays involve a detection reagent which is labeled with a fluorescent dye. The detection reagent is applied to an experimental sample, excited by a light source, and the number of photons emitted by the dye is measured by a detector with appropriate filters to restrict measurement to the fluorescence emission wavelength(s). The number of detected photons (fluorescence intensity) is correlated with the abundance of the analyte in the experimental sample. However, there are complicating factors that limit the reproducibility of fluorescence-based assays between laboratories and over time, even when using standardized reagents. The number of fluorescence photons detected per excited fluorophore is affected by many confounding factors, such as the type of fluorescent dye, the configuration of the instrument, the linearity of the detector, the stability of the fluorescent dye, the age of the instrument hardware, and the buffer pH at the time of measurement.

SUMMARY OF THE INVENTION

One embodiment of the present invention is a method for calibration and performance monitoring of a fluorescence detector, and a kit useful for carrying out such method comprising a set of populations of microbeads, at least two populations within said set containing different, highly uniform, determinable quantities of one or more non-overlapping internally-bound fluorescent dyes, and at least one population within said set containing a highly uniform, determinable quantity of one or more non-overlapping surface-bound fluorescent dyes. In some embodiments, the method involves the use of a fluorescent detection reagent, a fluorescence detector, and a microbead calibration kit. In some embodiments, the method comprises calibrating the cytometer in a traceable unit of measure by comparing each individual microbead population to reference solutions of a fluorescent dye and determining the mean equivalent reference fluorophores (ERF) or molecules of equivalent soluble fluorophores (MESF) of each population. In some embodiments, the method comprises comparing the detection reagent to reference solutions of fluorophore to determine the mean MESF per molecule of detection reagent. The reference solutions of fluorophore may then be measured using a fluorescence spectrophotometer, solution fluorimeter, or similar device. Microbeads lacking any fluorescent dyes, but being constructed of the same material as the other microbeads in the kit, may be measured using a fluorescence spectrophotometer, solution fluorimeter, or similar device to determine the autofluorescence of said material. The intensity of said autofluorescence may be subtracted from the intensity of another microbead population. In some embodiments, the method comprises measuring at least two internally-labeled microbead populations on a flow cytometer or fluorescence microscope, and creating a plot of the median fluorescence intensity (MFI) of the populations versus the separately calculated mean ERF of each population. A linear regression analysis of said plot is then performed, determining the equation of the regression line. At least one surface-labeled microbead population is then measured on said flow cytometer or fluorescence microscope, and the point at which the MFI of said microbead population intercepts said regression line is identified. In some embodiments, the method comprises rewriting the regression equation in terms of MFI versus MESF. The previously determined mean MESF per molecule of detection reagent may then be used to calculate a modified regression equation written in terms of MFI versus molecules of detection reagent. The modified regression equation may then be used to determine the number of molecules of detection reagent bound to and experimental sample in terms of molecules of detected analyte (MDA). In some embodiments, the method comprises mixing at least one internally-labeled microbead population with the experimental sample as "in-well control beads", and measuring the suspension of the experimental sample and microbeads on the instrument. The fluorescence intensity of said in-well control beads may be recorded over time. Instrument performance may then be monitored in real-time using said in-well control beads. In some embodiments, the method comprises a computer program or human operator using time-stamped data from in-well control beads to exclude from later analyses any experimental sample events that were acquired during a time period when the instrument was performing outside a user-specifiable performance range.

DETAILED DESCRIPTION OF THE INVENTION

Introduction

Figure 1:
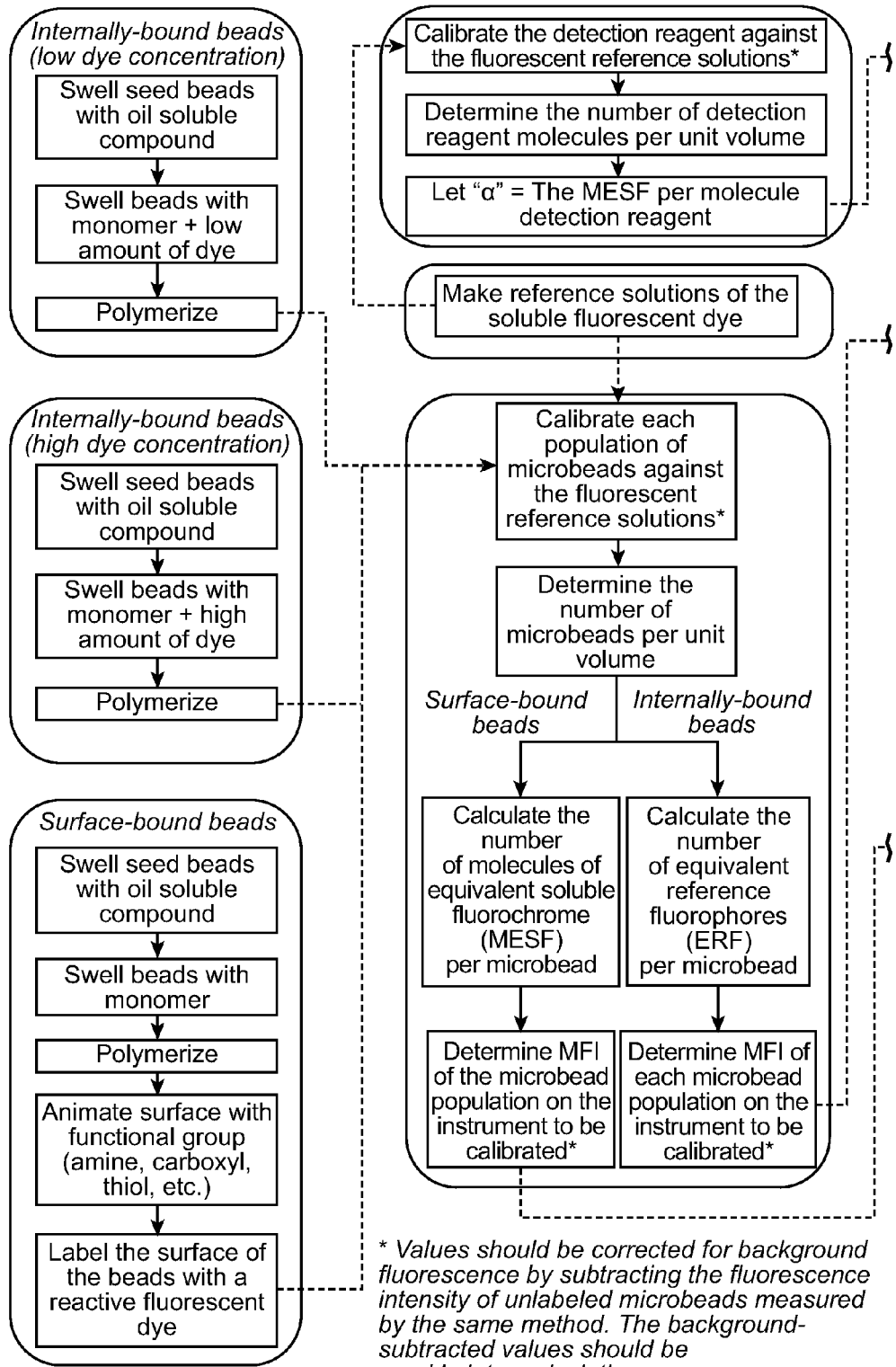
FIG. 1 is a block diagram of example steps involved in synthesizing the microbead kit described in an embodiment of the invention. Also described in an embodiment of the invention are the steps involved in the method of calibrating a fluorescence detector and measuring a sample in terms of MESF and MDA, using said kit.
Figure 1:
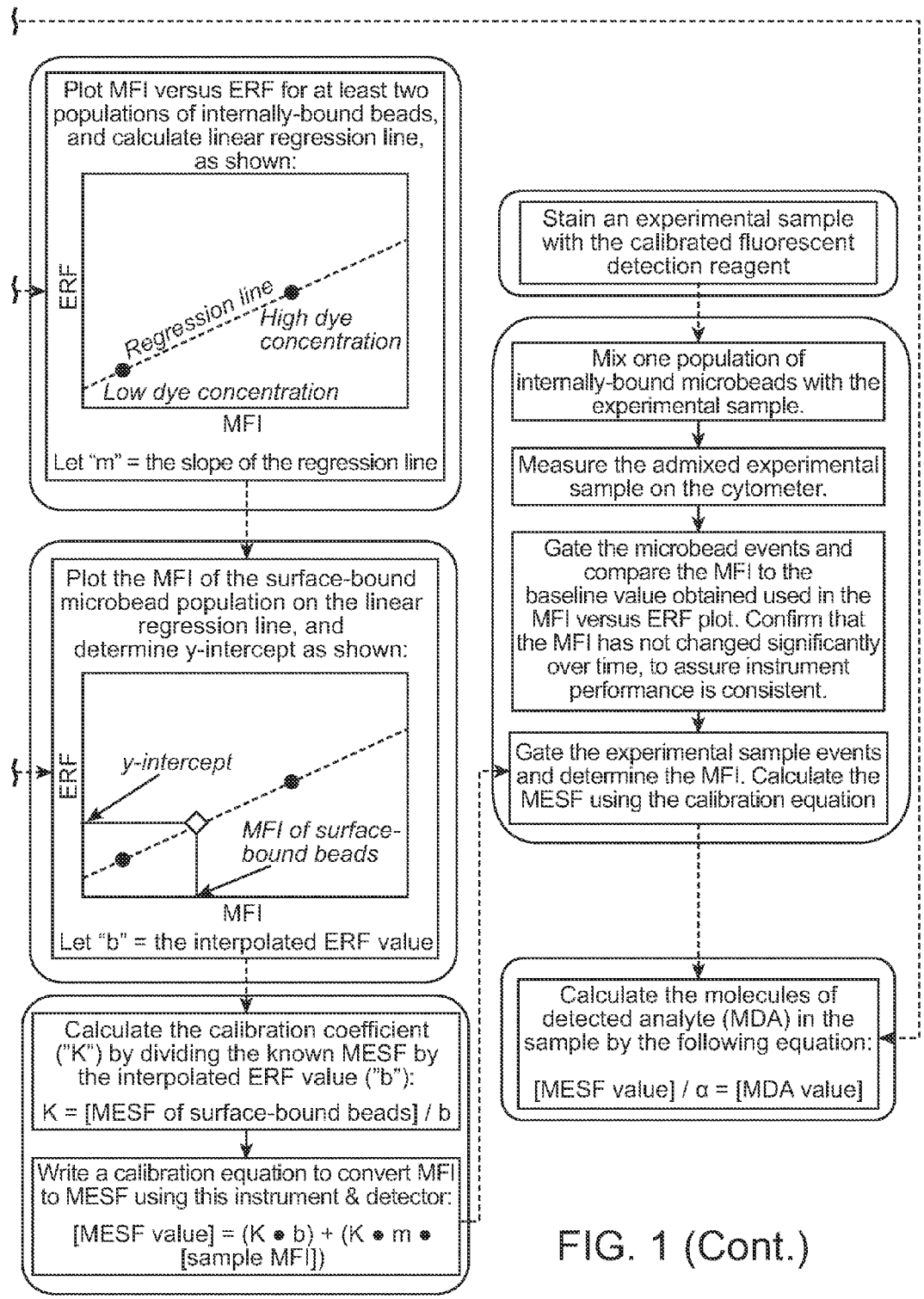

All publications, patents, and patent applications mentioned in this specification are herein incorporated by reference in their entirety for all purposes as well as for the proposition that each is recited to the same extent as if each individual publication, patent, or patent application was specifically and individually indicated to be incorporated by reference.

The present invention incorporates information disclosed in other applications and texts. The following publications are hereby incorporated by reference in their entireties: Shapiro, Practical Flow Cytometry, 4th Ed., John Wiley & Sons, 2003; Givan, Flow cytometry: first principles, 2nd Ed., John Wiley and Sons, 2001; Macey, Flow cytometry: principles and applications, Humana Press, 2007; Kenney, J. F. and Keeping, E. S., Mathematics of Statistics, 3rd ed., Van Nostrand, 1962. The following patent applications are also incorporated by reference in their entireties: U.S. Pat. Nos. 4,357,668; 4,609,689; 4,699,828; 4,704,891; 4,714,682; 4,767,206; 4,828,984; 4,857,451; 4,868,126; 4,868,126; 4,918,004; 4,918,004; 5,073,497; 5,073,498; 5,084,394; 5,089,416; 5,093,234; 5,144,224; 5,314,824; 5,380,663; 5,540,494; 5,620,842; 5,837,547; 6,074,879; 6,521,729; 6,542,833; 6,951,727; European Patent No. 0,511,314; and U.S. Ser. Nos. 10/326,524, now U.S. Pat. No. 6,897,954; Ser. No. 10/504,036, now abandoned; Ser. No. 10/865,664, now U.S. Pat. No. 6,906,792, and Ser. No. 11/303,350, now abandoned.

Some commercial reagents, protocols, software and instruments that are useful in some embodiments of the present invention are available at the Becton Dickinson website http://www.bdbiosciences.com/features/products/, and the Beckman Coulter website, http://www.beckmancoulter.com/Default.asp?bhfv=7.

The following relevant articles are incorporated by reference in their entireties: Wang et al., Quantitating Fluorescence Intensity From Fluorophores: Practical Use of MESF Values, J. Res. Natl. Inst. Stand. Technol. 107, 339-353 (2002); Wang et al., Toward Quantitative Fluorescence Measurements with Multicolor Flow Cytometry, Cytometry Part A, 73A: 279-288, 2008; Purvis and Stelzer. Multi-platform, multi-site instrumentation and reagent standardization. Cytometry. 33 (2), 156-65 (1998); Schwartz et al. Formalization of the MESF unit of fluorescence intensity. Cytometry Part B, Clinical cytometry. 57 (1), 1-6 (2004); Schwartz et al., Standardizing flow cytometry: construction of a standardized fluorescence calibration plot using matching spectral calibrators. Cytometry. 26 (1), 22-31 (1996); Schwartz et al. Standardizing flow cytometry: a classification system of fluorescence standards used for flow cytometry. Cytometry. 33 (2), 106-14 (1998); Schwartz et al., Quantitating Fluorescence Intensity from Fluorophore: The Definition of MESF Assignment, J. Res. Natl. Inst. Stand. Technol. 107, 83-91 (2002).

Experimental and process protocols and other helpful information can be found at Stanford University websites http://proteomics.stanford.edu and http://facs.stanford.edu. Patents and applications that are also incorporated by reference include U.S. Pat. Nos. 7,381,535 and 7,393,656 and U.S. Ser. No. 10/193,462, now U.S. Pat. No. 7,563,584; Ser. No. 11/655,785, now U.S. Pat. No. 7,695,924; Ser. No. 11/655,789, now abandoned: Ser. No. 11/655,821, now U.S. Pat. No. 7,695,924; Ser No. 11/338,957, now pending, Ser. Nos. 61/048,886; 61/048,920; and 61/048,657, now expired.

Before describing the present invention in detail, it is to be understood that this invention is not limited to particular methods, devices, or systems, which can, of course, vary. It should also be understood that the detailed description and the specific examples, while indicating specific embodiments, are given by way of illustration only, since various changes and modifications within the spirit and scope of the invention will become apparent to those skilled in the art from this detailed description. It is also to be understood that the terminology used herein is for the purpose of describing particular embodiments only, and is not intended to be limiting. In addition, unless defined otherwise, all technical and scientific terms used herein have the same meaning as commonly understood by one of ordinary skill in the art to which the invention pertains. Furthermore, it is to be understood that although the methods, systems, and other aspects of the invention are described herein, for purposes of clarity of illustration, with particular reference to flow cytometry, such reference is not intended to be limiting. Headings of sections provided in this patent application and the title of this patent application are for convenience only, and are not to be taken as limiting the disclosure in any way.

Some characteristics of embodiments of the present invention are presented in a range format in which one series of numbers is presented as a lower FIGURE and another as an upper FIGURE. It is intended that any of the lower FIGUREs can be combined with any of the upper FIGUREs to present an appropriate range.

Manufacture of Microbeads

One embodiment of the present invention includes a calibration kit which comprises several populations of fluorescent microbeads, at least one population being surface-dyed microbeads containing one or more non-overlapping fluorescent dyes, and at least two populations being internally-dyed microbeads with different amounts of one or more non-overlapping fluorescent dyes. By the terms "microbead", "bead", or "particle" as used herein is meant any solid particle, of virtually any shape, suitable for measurement by a fluorescence instrument. By "fluorescent dye" as used herein is meant any dye, molecule, complex, or particle that may be excited by a given wavelength of electromagnetic radiation, and emit photons of another wavelength. It should be understood that the terms "fluorescent dye", "fluorescent probe", "fluorescent molecule", "fluorophore", "fluorochrome", "fluorescent nanocrystal", and grammatical equivalents thereof, may be used interchangeably herein to refer to a fluorescent dye. By "overlapping" as used herein is meant when excited by any given wavelength of light, a first fluorescent dye emits some photons with the same wavelength as those emitted by a second fluorescent dye. Microbeads containing multiple overlapping fluorescent dyes have different fluorescence excitation and emission spectra depending on the number of molecules of dye per bead, as illustrated by Wang et al., Cytometry (2008). Consequently, the disclosed invention comprises calibration microbeads with one or more non-overlapping fluorescent dyes, so the excitation and emission spectra are comparable between bright and dim microbeads, and therefore the slope and linearity of the detector can be accurately determined.

Fluorophores can be either "small molecule" fluors, or proteinaceous fluors (e.g. green fluorescent proteins and all variants thereof). Suitable fluorophores include, but are not limited to, 1,1'-diethyl-2,2'-cyanine iodide, 1,2-diphenylacetylene, 1,4-diphenylbutadiene, 1,6-Diphenylhexatriene, 2-Methylbenzoxazole, 2,5-Diphenyloxazole (PPO), 4-(dicyanomethylene)-2-methyl-6-(p-dimethylaminostyryl)-4H-pyran (DCM), 4-Dimethylamino-4'-nitrostilbene, 4',6-Diamidino-2-phenylindole (DAPI), 5-ROX, 7-AAD, 7-Benzylamino-4-nitrobenz-2-oxa-1,3-diazole, 7-Methoxycoumarin-4-acetic acid, 9,10-Bis(phenylethynyl)anthracene, 9,10-Diphenylanthracene, Acridine Orange, Acridine yellow, Adenine, Allophycocyanin (APC), AMCA, AmCyan, Anthracene, Anthraquinone, APC, Auramine O, Azobenzene, Benzene, Benzoquinone, Beta-carotene, Bilirubin, Biphenyl, BO-PRO-1, BOBO-1, BODIPY FL, Calcium Green-1, Cascade Blue™, Cascade Yellow™, Chlorophyll a, Chlorophyll b, Chromomycin, Coumarin, Coumarin 1, Coumarin 30, Coumarin 314, Coumarin 343, Coumarin 6, Cresyl violet perchlorate, Cryptocyanine, Crystal violet, Cy2, Cy3, Cy3.5, Cy5, Cy5.5, Cy7, Cytosine, DA, Dansyl glycine, DAPI, DiI, DiO, DiOCn, Diprotonated-tetraphenylporphyrin, DsRed, EDANS, Eosin, Erythrosin, Ethidium Monoazide, Ethyl p-dimethylaminobenzoate, FAM, Ferrocene, FI, Fluo-3, Fluo-4, Fluorescein, Fluorescein isothiocyanate (FITC), Fura-2, Guanine, HcRed, Hematin, Histidine, Hoechst, Hoechst 33258, Hoechst 33342, IAEDANS, Indo-1, Indocarbocyanine (C3)dye, Indodicarbocyanine (C5)dye, Indotricarbocyanine (C7)dye, LC Red 640, LC Red 705, Lucifer yellow, LysoSensor Yellow/Blue, Magnesium octaethylporphyrin, Magnesium octaethylporphyrin (MgOEP), Magnesium phthalocyanine (MgPc), Magnesium tetramesitylporphyrin (MgTMP), Magnesium tetraphenylporphyrin (MgTPP), Malachite green, Marina Blue®, Merocyanine 540, Methyl-coumarin, MitoTracker Red, N,N'-Difluoroboryl-1,9-dimethyl-5-(4-iodophenyl)-dipyrrin, N,N'-Difluoroboryl-1,9-dimethyl-5-[(4-(2-trimethylsilylethynyl), N,N'-Difluoroboryl-1,9-dimethyl-5-phenydipyrrin, Naphthalene, Nile Blue, Nile Red, Octaethylporphyrin, Oregon green, Oxacarbocyanine (C3) dye, Oxadicarbocyanine (C5)dye, Oxatricarbocyanine (C7) dye, Oxazine 1, Oxazine 170, p-Quaterphenyl, p-Terphenyl, Pacific Blue®, Peridinin chlorophyll protein complex (PerCP), Perylene, Phenol, Phenylalanine, Phthalocyanine (Pc), Pinacyanol iodide, Piroxicam, POPOP, Porphin, Proflavin, Propidium iodide, Pyrene, Pyronin Y, Pyrrole, Quinine sulfate, R-Phycoerythrin (PE), Rhodamine, Rhodamine 123, Rhodamine 6G, Riboflavin, Rose bengal, SNARF®, Squarylium dye III, Stains-all, Stilbene, Sulforhodamine 101, SYTOX Blue, TAMRA, Tetra-t-butylazaporphine, Tetra-t-butylnaphthalocyanine, Tetrakis(2,6-dichlorophenyl)porphyrin, Tetrakis(o-aminophenyl)porphyrin, Tetramesitylporphyrin (TMP), tetramethylrhodamine, Tetraphenylporphyrin (TPP), Texas Red® (TR), Thiacarbocyanine (C3)dye, Thiadicarbocyanine (C5)dye, Thiatricarbocyanine (C7)dye, Thiazole Orange, Thymine, TO-PRO®-3, Toluene, TOTO-3, TR, Tris(2,2'-bipyridyl(ruthenium(II), TRITC, TRP, Tryptophan, Tyrosine, Uracil, Vitamin B12, YO-PRO-1, YOYO-1, Zinc octaethylporphyrin (ZnOEP), Zinc phthalocyanine (ZnPc), Zinc tetramesitylporphyrin (ZnTMP), Zinc tetramesitylporphyrin radical cation, and Zinc tetraphenylporphyrin (ZnTPP). Suitable optical dyes are described in the 1996 Molecular Probes Handbook by Richard P. Haugland, hereby expressly incorporated by reference.

In some embodiments, the fluorescent dye may be an Alexa Fluor® dye, including Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750 (Life Technologies Corporation (formerly Invitrogen), 5791 Van Allen Way, Carlsbad, Calif. 92008).

In some embodiments, the fluorescent dye may be a tandem fluorophore conjugate, including Cy5-PE, Cy5.5-PE, Cy7-PE, Cy5.5-APC, Cy7-APC, Cy5.5-PerCP, Alexa Fluor® 610-PE, Alexa Fluor® 700-APC, and Texas Red-PE. Tandem conjugates are less stable than monomeric fluorophores, so comparing a detection reagent labeled with a tandem conjugate to reference solutions may yield MESF calibration constants with less precision than if a monomeric fluorophore had been used.

In some embodiments, the fluorescent dye may be a fluorescent protein such as green fluorescent protein (GFP; Chalfie, et al., Science 263(5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H1 J9; 2. Stauber, R. H. Biotechniques 24(3):462-471 (1998); 3. Heim, R. and Tsien, R. Y. Curr. Biol. 6:178-182 (1996)), cyan fluorescent protein (CFP), and enhanced yellow fluorescent protein (EYFP; 1. Clontech Laboratories, Inc., 1020 East Meadow Circle, Palo Alto, Calif. 94303). In some embodiments, the fluorescent dye is dTomato, FlAsH, mBanana, mCherry, mHoneydew, mOrange, mPlum, mStrawberry, mTangerine, ReAsH, Sapphire, mKO, mCitrine, Cerulean, Ypet, tdTomato, Emerald, or T-Sapphire (Shaner et al., Nature Methods, 2(12):905-9. (2005)). All of the above-cited references are expressly incorporated herein by reference.

In some embodiments, the fluorescent dye may be a fluorescent semiconductor nanocrystal particle, or quantum dot, including Qdot® 525 nanocrystals, Qdot® 565 nanocrystals, Qdot® 585 nanocrystals, Qdot® 605 nanocrystals, Qdot® 655 nanocrystals, Qdot® 705 nanocrystals, Qdot® 800 nanocrystals (Life Technologies Corporation (formerly Invitrogen), 5791 Van Allen Way, Carlsbad, Calif. 92008). In some embodiments, the fluorescent dye may be an upconversion nanocrystal, as described in Wang et al., Chem. Soc. Rev., 38:976-989 (2009), which is hereby incorporated by reference in its entirety.

In some embodiments of the invention, fluorescent molecules (fluorophores) may be conjugated with antibodies or other detection reagents, and associated with components of a sample that is analyzed by the instrument. Fluorophores can be activated by light from the instrument and re-emit light of a different wavelength. Since antibodies bind to antigens on the cells, the amount of light detected from the fluorophores is related to the number of antigens associated with the cell passing through the beam. In another embodiment of the invention, a fluorescently-labeled DNA oligonucleotide can be associated with the genomic DNA of a cell, and the amount of light detected from the fluorophores is related to the number of copies of the oligonucleotide that have hybridized to complimentary regions in the genome. Any specific set of fluorescently tagged detection reagents in any embodiment can depend on the types of experimental samples to be studied.

Several fluorescent detection reagents can be used simultaneously, so measurements made as one cell passes through the laser beam consist of scattered light intensities as well as light intensities from each of the fluorophores. Thus, the characterization of a single cell can consist of a set of measured light intensities that may be represented as a coordinate position in a multidimensional space. Considering only the light from the fluorophores, there is one coordinate axis corresponding to each of the fluorescently tagged detection reagents. The number of coordinate axes (the dimension of the space) is the number of fluorophores used. Modern flow cytometers can measure several colors associated with different fluorophores and thousands of cells per second. Thus, the data from one subject can be described by a collection of measurements related to the number of antigens for each of (typically) many thousands of individual cells. See U.S. Pat. Nos. 7,381,535 and 7,393,656 for examples of flow cytometry methods and applications, which are hereby incorporated by reference in their entirety.

Microbeads may be manufactured using any of the methods known in the art. In some embodiments of the present invention, internally-dyed microbeads may be manufactured following the copolymerization methods described in U.S. Pat. No. 5,073,498. In some embodiments of the present invention, surface-dyed microbeads may be manufactured using methods described in U.S. Pat. No. 4,609,689; 4,157,323; 4,285,819 or 4,326,008. In some embodiments of the present invention, microbeads may be comprised of a polymeric seed particle and one or more monomeric swelling agents. In some embodiments of the present invention, microbeads may be substantially spherical, with a diameter between 0.5, 1, 5, 10, microns and 50, 60, 70 and 100 microns. In some embodiments of the present invention, microbeads may have a refractive index between 1.0, 1.1, 1.2, 1.3, and 1.6, 1.7, 1.8, 1.9, and 2.0. In some embodiments of the present invention, microbeads may be fabricated from hydrophobic materials including polystyrene, polyacrylamide, latex, polyvinylchloride, polypropylene, polyethylene, polylactic acid, etc. In some embodiments of the present invention, microbeads may be obtained from commercial suppliers, including: Bangs Laboratories, Inc, 9025 Technology Drive, Fishers, Ind. 46038-2886; Life Technologies Corporation (formerly Invitrogen), 5791 Van Allen Way, Carlsbad, Calif. 92008; Brookhaven Instruments Limited, Chapel House, Stock Wood Redditch, Worcestershire B96 6ST, UK; Spherotech, Inc., 27845 Irma Lee Circle, Unit 101, Lake Forest, Ill. 60045; Polysciences, Inc., 400 Valley Road, Warrington, Pa. 18976; BD, 1 Becton Drive, Franklin Lakes, N.J., 07417.

Microbeads may be any shape. In some embodiments of the present invention, microbeads may be irregularly shaped, or substantially spherical, cubic, rhomboid, tetragonal, dodecahedral, ovoid, cylindrical, etc. Microbeads may have any surface texture. In some embodiments of the present invention, microbeads may have surfaces that are substantially smooth, dimpled, wrinkled, angled, etc.

In some embodiments of the present invention, the conjugation reaction used to attach fluorescent dyes to the surface of microbeads may involve fluorophores functionalized with reactive groups, including amine-, carboxyl-, and thiol-reactive groups. In some embodiments of the present invention, the surface of microbeads may be functionalized with a molecule suitable for conjugation, including epoxy, amine, sulfhydryl, or carboxyl groups. In some embodiments of the present invention, click chemistry reactions, such as azide-alkyne Huisgen cycloaddition, may be used to attach fluorescent dyes to the surface of microbeads. Examples of click chemistry reactions are described in Kolb et al., Angewandte Chemie International Edition 40 (11): 2004-2021 (2001), which is hereby incorporated by reference in its entirety.

In some embodiments of the present invention, several populations of microbeads may be manufactured with different fluorescent dyes and provided as a kit to be used to calibrate more than one detector on an instrument. In this embodiment, it is desirable that each microbead population be highly uniform (i.e. less than 0.5%, 1%, 2%, 5%, or 10% CV) in terms of diameter, refractive index, and number of molecules of dye per bead. In some embodiments, microbeads may contain a plurality of non-overlapping fluorescent dyes. Microbeads containing more than one overlapping dye exhibit different spectral properties depending on the relative abundance of each dye (Wang et al., 2008). Thus special care must be taken to select dyes that are non-overlapping, if more than one dye is to be incorporated into a single microbead. In some embodiments, several populations of microbeads may distinguishable by spectral properties which do not interfere with the excitation and emission spectra of the calibrated dye, including one or more non-overlapping dyes, diameter, refractive index, reflectivity, fluorescence intensity, light scatter, and Raman spectrum.

In some embodiments of the methods of the invention, several spectrally-distinguishable populations may be provided in a heterogeneous suspension, or provided as several homogeneous suspensions to be combined immediately before analysis, then measured using a single-particle analysis platform such as a flow cytometer or fluorescence microscope. Furthermore, the fluorescence intensity of each population may be determined by restricting the analysis (gating) based on the spectral properties of the particles in one or more dimensions. In some embodiments of the methods of the invention, some steps of the analysis process may be automatically performed by computer software, including: Gating microbead populations, calculation of MFI, calculation of ERF, referencing an experimentally determined MESF value, linear regression analysis, calculation of a calibration constant, and display of data in calibrated units.

Fluorescent Detection Reagents

By "detection reagent", as used herein, is meant any molecule, or complex of molecules, with a specific binding affinity for an analyte of interest. In some embodiments, the detection reagent may be conjugated to a fluorescent dye. By "fluorescent detection reagent" as used herein is meant any detection reagent which possesses fluorescent properties, or which is conjugated to a fluorescent dye. Depending on the molecular structure of the detection reagent, fluorescent dyes may be conjugated to different functional groups. Suitable functional groups for conjugation include, but are not limited to, amino groups, carboxy groups, maleimide groups, oxo groups and thiol groups, with amino groups and thiol groups being particularly preferred. For example, fluorescent dyes containing amino groups can be attached to detection reagents containing amino groups using cross-linkers as are known in the art; for example, homo- or hetero-bifunctional cross-linkers as are well known (see 1994 Pierce Chemical Company catalog, technical section on cross-linkers, pages 155-200, incorporated herein by reference).

When preparing a batch of fluorescent detection reagent, it is beneficial to purify the labeled detection reagent away from any unlabeled detection reagent or unbound fluorescent dye. When a solution of fluorescent detection reagent is applied to an experimental sample, any unlabeled detection reagent molecules may compete for binding, thereby reducing the amount of detectable signal. When a solution of fluorescent detection reagent is applied to an experimental sample, any unbound fluorescent dye molecules may react non-specifically with the sample, thereby increasing the amount of detectable noise or background. Different methods of purification are well known in the art, including affinity column purification, size-exclusion chromatography, ion-exchange chromatography, high-pressure liquid chromatography, size-exclusion membrane filtration, protein A conjugation, centrifugation, ultracentrifugation, etc.

In some embodiments, each molecule of detection reagent may be conjugated to more than 1, 2, 3, 4, 5, 6, 7, 8, 9, 10, 20, 50, or 100 molecules of fluorescent dye. For example, it is common in the art for a monoclonal antibody to be conjugated to between 4 and 10 molecules of fluorescent dye.

In some embodiments, each molecule of fluorescent dye may be conjugated to more than 1, 2, 3, 4, 5, 6, 7, 8, 9, 10, 20, 50, or 100 molecules of detection reagent. For example, it is common in the art for a quantum dot to be conjugated to between 2 and 20 molecules of a monoclonal antibody.

In some embodiments, the detection reagent may be a peptide, polypeptide, oligopeptide or a protein. The peptide, polypeptide, oligopeptide or protein may be made up of naturally occurring amino acids and peptide bonds, or synthetic peptidomimetic structures. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. 5218: U138 Part 2 Aug. 22, 1999, both of which are expressly incorporated by reference herein.

In some embodiments, the detection reagent is an antibody. In some embodiments, the detection reagent is an activation state-specific antibody. In some embodiments, the detection reagent is a phospho-specific antibody.

The term "antibody" includes full length antibodies and antibody fragments, and may refer to a natural antibody from any organism, an engineered antibody, or an antibody generated recombinantly for experimental, therapeutic, or other purposes as further defined below. Examples of antibody fragments, as are known in the art, such as Fab, Fab', F(ab')$_2$, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory. The antibodies of the present invention may be nonhuman, chimeric, humanized, or fully human. For a description of the concepts of chimeric and humanized antibodies see Clark et al., 2000 and references cited therein (Clark, (2000) Immunol. Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In some embodiments, the antibodies of the present invention are humanized.

Many antibodies, many of which are commercially available (for example, see Cell Signaling Technology, www.cellsignal.com, Millipore, eBioscience, Caltag, Santa Cruz Biotech, Abcam, BD Biosciences, Sigma and Anaspec, the contents of which are incorporated herein by reference) have been produced which specifically bind to the phosphorylated isoform of a protein but do not specifically bind to a non-phosphorylated isoform of a protein. In some embodiments, the detection reagent may be an isoform-specific antibody.

In some embodiments, the detection reagent may be a non-activation state antibody. In some embodiments, non-activation state antibodies bind to epitopes in both activated and non-activated forms of an element.

In some embodiments, the detection reagent may be a peptide comprising a recognition structure that binds to a target structure on an activatable protein.

In some embodiments the detection reagent may be a nucleic acid. The term "nucleic acid" as used herein is meant to include nucleic acid analogs, for example, phosphoramide (Beaucage et al., (1993) Tetrahedron 49(10):1925 and references therein; Letsinger, J. (1970) Org. Chem. 35:3800; Sprinzl et al., (1977) Eur. J. Biochem. 81:579; Letsinger et al., (1986) Nucl. Acids Res. 14:3487; Sawai et al, (1984) Chem. Lett. 805, Letsinger et al., (1988) J. Am. Chem. Soc. 110: 4470; and Pauwels et al., (1986) Chemica Scripta 26:141-9), phosphorothioate (Mag et al., (1991) Nucleic Acids Res. 19:1437; and U.S. Pat. No. 5,644,048), phosphorodithioate (Briu et al., (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm, (1992) J. Am. Chem. Soc. 114:1895; Meier et al., (1992) Chem. Int. Ed. Engl. 31:1008; Nielsen, (1993) Nature, 365:566; Carlsson et al., (1996) Nature 380:207, all of which are incorporated by reference).

In some embodiments, the detection reagent may be a synthetic compound. Any numbers of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

Alternatively, in some embodiments the detection reagent may be a natural compound, in the form of bacterial, fungal, plant and animal extracts that are available or readily produced.

Additionally, natural or synthetically produced compounds are readily modified through conventional chemical, physical and biochemical means. Known pharmacological agents may be subjected to directed or random chemical modifications, including enzymatic modifications, to produce detection reagents that may be used in the instant invention.

In some embodiment the detection reagent may be a small organic compound. Detection reagents can be synthesized from a series of substrates that can be chemically modified. "Chemically modified" herein includes traditional chemical reactions as well as enzymatic reactions.

In some embodiments the detection reagent may be a carbohydrate. As used herein the term carbohydrate is meant to include any compound with the general formula $(CH2O)n$. Examples of carbohydrates are di-, tri- and oligosaccharides, as well polysaccharides such as glycogen, cellulose, and starches.

In some embodiments the detection reagent may be a lipid. As used herein the term lipid is meant to include any water insoluble organic molecule that is soluble in nonpolar organic solvents. Examples of lipids are steroids, such as cholesterol, and phospholipids such as sphingomyelin.

Assignment of MESF or ERF Values

To reliably compare of fluorescence measurements between different laboratories, instruments, and over time, fluorescence data should be converted to a standardized unit of measure. Molecules of equivalent soluble fluorophore (MESF) is a traceable unit of measure recognized by the United States National Institute of Standards and Technology. See U.S. Pat. No. 4,767,206 and Schwartz et al., J. Res. Natl. Inst. Stand. Technol. 107, 83-91 (2002) for more details on the calculation of MESF. Storing and communicating data in terms of MESF is particularly useful in clinical research and diagnosis environments. The use of MESF and standardized reagents would allow standardized definitions of different human pathologies in terms of MESF. Standardized definitions in clinical flow cytometry would allow quantitative comparison of data between laboratories around the world, as well as retrospective comparison to recorded values over time, independent of operator bias and instrument configurations. The use of MESF measurements in applications where flow cytometry is used as a diagnostic or prognostic assay (see U.S. Pat. App. No. 2009/0098594) would increase the robustness of such assays, and may facilitate or expedite approval by governmental regulatory bodies.

Generally, the calculation of MESF begins with determining the exact concentration of a reference solution of a fluorophore (e.g. fluorescein). The exact concentration may be determined by a multitude of methods, including enzymatic co-labeling, radiolabeling, peptide mass spectrometry, elemental mass spectrometry, mass cytometry, high pressure liquid chromatography; protein sequencing, Edman degradation, etc. A dilution series of the reference solution may then be measured on an instrument capable of measuring fluorescence, such as a fluorescence spectrophotometer, solution fluorimeter, etc. The results of these measurements may be used to construct a standard curve, or a regression equation, which correlates a given measured fluorescent intensity with an exact number of soluble reference fluorophores, thereby calibrating the instrument in terms of MESF. A sample containing on its surface an unknown quantity of the same fluorophore may be measured on the same instrument, and the molecules of equivalent soluble fluorophore of the sample may be calculated. If the sample is a suspension of independent elements, such as particles, cells, or molecules, then the MESF of the solution may be divided by the concentration of the objects to determine the mean MESF per element.

In some embodiments, the MESF per molecule of detection reagent in a solution may be determined by dividing the MESF of the solution by the molecular concentration of the detection reagent. In some embodiments, the MESF per molecule of detection reagent may be estimated by calculating the fluorophore-to-protein ratio by the steps comprising: Measuring the labeled detection reagent solution using an absorbance spectrophotometer; calculating the concentration of protein using the known extinction coefficient of the protein; calculating the concentration of the fluorescent dye using the known extinction coefficient of the fluorescent dye; assuming each molecule of fluorescent dye has a given MESF (e.g. 0.90, 0.95, 1.0, etc.). It is preferable to calculate the MESF of a detection reagent by comparison to reference solutions instead of estimating the MESF by means of absorbance spectrophotometry. Although the fluorophore-to-protein ratio may often be calculated accurately by absorbance spectrophotometry, due to intramolecular interactions in the reagent-dye conjugate, the fluorescence intensity of each conjugated fluorophore is not necessarily identical to the fluorescence intensity of the same fluorophore in solution, so the MESF per fluorophore may not necessarily be equal to 1.0.

Fluorophores impregnated within a solid substrate may exhibit different fluorescence excitation and emission properties than soluble fluorophores under the same conditions. Therefore, although internally-labeled particles may be compared to reference solutions of fluorophores using the MESF-determination methods described above, the fluorescence intensity is not necessarily an indication of the exact number of fluorophores, and therefore a MESF value can not be determined (Wang et al., Cytometry Part A, 73A: 279-288, 2008). Instead, one may describe the intensity of an internally-labeled particle in terms of the number of equivalent reference fluorophores (ERF), following Wang et al., Cytometry Part A, 73A: 279-288, 2008. ERF, like MESF, increases linearly with the number of fluorophores contained in the particle. Since the emission spectra of reference fluorophores are generally narrow, it is assumed that the entire emission spectrum of the reference solution is integrated for calculations of MESF and ERF. However, since dyes with broad emission spectra are frequently incorporated into particles, ERF calculations are scaled to the fraction of the particle's emission spectrum that is measured. One may use a series of beads with known ERF values to assess the slope and linearity of a fluorescence detector (Wang et al., Cytometry Part A, 73A: 279-288, 2008).

In some embodiments, reference solutions of a fluorophore in solution at known concentrations will be obtained, said fluorophore being the same fluorophore that was used to label the detection reagent and at least one population of surface-labeled microbeads provided in the calibration kit.

Fluorescence in a solution can be measured using a fluorimeter, fluorescence spectrophotometer, etc. In general, excitation radiation, from an excitation source having a first wavelength, passes through excitation optics. The excitation optics cause the excitation radiation to excite the sample. In response, fluorescent dyes or particles in the sample emit radiation that has a wavelength that is different from the excitation wavelength. Collection optics then collect the emission from the sample. The device can include a temperature controller to maintain the sample at a specific temperature while it is being scanned.

In some embodiments, the MESF of a population of surface-labeled microbeads may be determined. The fluorescence intensity of a series of reference solutions of soluble fluorophore may be measured using a fluorescence spectrophotometer or similar device. Then, the observed fluorescence intensity of each reference solution may be plotted versus the known concentration of soluble fluorophore, and a linear regression equation determined by the least-squares method (Kenney and Keeping, 1962). A suspension of surface-labeled microbeads may be measured using a volumetric counting device such as a Coulter Counter™, hemocytometer, or flow cytometer with a TruCount™ tube to determine the number of surface-labeled microbeads per unit volume. The fluorescence intensity of a population of surface-labeled microbeads and a population of unlabeled microbeads may then be measured using the same fluorescence spectrophotometer as above. The background-subtracted fluorescence intensity of the population of surface-labeled microbeads may be calculated by subtracting the fluorescence intensity of the unlabeled microbeads from the raw fluorescence intensity of the surface-labeled microbeads. The MESF of the surface-labeled microbead population may then be interpolated from the background-subtracted fluorescence intensity, using the linear regression equation calculated from the reference solutions, above. The MESF per microbead may then be determined by dividing the MESF of the microbead suspension by the concentration of microbeads in the suspension. A value of MESF per microbead may be assigned to the same lot of surface-labeled microbead suspension, and this value may be provided with the kit to the end user. In some embodiments, the MESF per microbead value is provided by means of a written product insert, on a barcode, on a digital data disk, as part of a software program, as a downloadable software component, or by remote broadcast, such as over the Internet. In some embodiments, the MESF per microbead value may be updated dynamically as the microbead suspension ages and is recalibrated to fluorophore reference solutions.

In some embodiments, the ERF of a population of internally-labeled microbeads may be determined. The fluorescence intensity of a series of reference solutions of soluble fluorophore may be measured using a fluorescence spectrophotometer or similar device. Then, the observed fluorescence intensity of each reference solution may be plotted versus the known concentration of soluble fluorophore, and a linear regression equation determined by the least-squares method (Kenney and Keeping, 1962). A suspension of internally-labeled microbeads may be measured using a volumetric counting device such as a Coulter Counter™, hemocytometer, or flow cytometer with a TruCount™ tube to determine the number of internally-labeled microbeads per unit volume. The fluorescence intensity of a population of internally-labeled microbeads and a population of unlabeled microbeads may then be measured using the same fluorescence spectrophotometer as above. The background-subtracted fluorescence intensity of the population of internally-labeled microbeads may be calculated by subtracting the fluorescence intensity of the unlabeled microbeads from the raw fluorescence intensity of the internally-labeled microbeads. The ERF of the internally-labeled microbead population may then be interpolated from the background-subtracted fluorescence intensity, using the linear regression equation calculated from the reference solutions, above. The ERF per microbead may then be determined by dividing the ERF of the microbead suspension by the concentration of microbeads in the suspension. A value of ERF per microbead may be assigned to the same lot of internally-labeled microbead suspension, and this value may be provided with the kit to the end user. In some embodiments, the ERF per microbead value is provided by means of a written product insert, on a barcode, on a digital data disk, as part of a software program, as a downloadable software component, or by remote broadcast, such as over the Internet. In some embodiments, the ERF per microbead value may be updated dynamically as the microbead suspension ages and is recalibrated to fluorophore reference solutions.

In some embodiments, the MESF of a solution of a species of fluorescent detection reagent may be determined. The fluorescence intensity of a series of reference solutions of soluble fluorophore may be measured using a fluorescence spectrophotometer or similar device. Then, the observed fluorescence intensity of each reference solution may be plotted versus the known concentration of soluble fluorophore, and a linear regression equation determined by the least-squares method (Kenney and Keeping, 1962). The concentration of a solution of fluorescent detection reagent may be measured using a suitable method to determine the number of molecules of fluorescent detection reagent per unit volume in the solution. Depending on the type of detection reagent, suitable methods may include spectrophotometry, mass spectrometry, high pressure liquid chromatography, ELISA, gel electrophoresis, amino acid sequencing, surface plasmon resonance, etc. The fluorescence intensity of a solution of fluorescent detection reagent and a population of unlabeled microbeads may then be measured using the same fluorescence spectrophotometer as above. The MESF of the solution of fluorescent detection reagent may then be interpolated from the fluorescence intensity, using the linear regression equation calculated from the reference solutions, above. The MESF per molecule of fluorescent detection reagent may then be determined by dividing the MESF of the solution of detection reagent by the concentration of the solution. A value of MESF per molecule of fluorescent detection reagent may be assigned to the same lot of fluorescent detection reagent solution, and this value may be provided with the kit to the end user. In some embodiments, the MESF per molecule of fluorescent detection reagent value is provided by means of a written product insert, on a barcode, on a digital data disk, as part of a software program, as a downloadable software component, or by remote broadcast, such as over the Internet. In some embodiments, the MESF per molecule of fluorescent detection reagent value may be updated dynamically as detection reagent solution ages and is recalibrated to fluorophore reference solutions.

Measurement of the Beads on the Instrument to be Calibrated

There are multiple ways to obtain fluorescence data that can be associated with cells or microbeads. In one embodiment of the invention flow cytometry is used to acquire fluorescence data. It is a technique for counting, examining, and sorting microscopic particles suspended in a stream of fluid. Flow cytometry allows simultaneous multi-parametric analysis of the physical and/or chemical characteristics of particles flowing through an optical and/or electronic detection apparatus. A liquid stream in the cytometer carries and aligns individual particles so that they pass through a laser beam in single file. As a particle passes through a light beam (usually laser light), light is scattered from the surface. Photomultiplier tubes collect the light scattered in the forward and side directions which gives information related to the particle size and shape. This information may be used to identify distinct populations of beads or cells (e.g. monocyte, lymphocyte, or granulocyte.) Modern flow cytometers can consist of multiple light sources and detectors. See Perfetto et al., Nature Reviews Immunology, 4:648-655 (2004), for a discussion of modern flow cytometers, which is hereby incorporated by reference in its entirety.

The data generated by flow-cytometers can be plotted in a single dimension, e.g. as a histogram, or in two dimensional, e.g. as a dot plots, or even in three, four, five, six, seven, eight or more dimensions. The regions on these plots can be sequentially separated, based on fluorescence intensity, by creating a series of subset extractions, termed "gates". Specific gating protocols exist for diagnostic and clinical purposes as well as other purposes. The plots are often made on logarithmic scales. Because different fluorescent dyes' emission spectra may overlap, signals from different detectors may be compensated electronically as well as computationally. Applications can then be used to compare data sets in order to distinguish two or more classes forming sub-populations within the data. Such analysis employs a number of computational tools. FlowJo (TreeStar Inc., Ashland, Oreg.) is one popular software tool used to analyze flow cytometry data. See U.S. Ser. No. 61/079,579 for gating analysis.

In some embodiments, different types of fluorescent monitoring systems capable of distinguishing individual particles, e.g., cytometric measurement device systems, may be used to practice the invention. In some embodiments, flow cytometric systems, microfluidic systems, confocal microscopes, or epifluorescence microscopes may be used to practice the invention. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

In some embodiments, the instrumentation may include optical elements, which can be a wide variety of different optical elements, depending on the labels and assay. In some embodiments, useful optical elements include lamps to excite fluorescent dyes; lasers to excite fluorescent dyes; dichroic mirrors to reflect wavelengths of light shorter than a certain threshold while permitting longer wavelengths of light to pass through; bandpass filters to attenuate wavelengths of light outside a given frequency range; and diffraction gratings or prisms to spatially disperse a light spectrum.

In some embodiments, the instrumentation may include a detector, which can be a wide variety of different detectors, depending on the labels and assay. In some embodiments, useful detectors include a flow cytometer or microscope with one or more channels of detection; photomultiplier tubes to detect and amplify the signal from photons and convert the signal into an electric current; CCD cameras to capture and transform data and images into quantifiable formats; and a computer workstation.

In some embodiments, a plurality of microbead populations may be measured successively on the instrument as separate, homogeneous solutions.

In some embodiments, a plurality of microbead populations, having spectral properties that are sufficiently different from each other to allow reliable discrimination thereof, may be provided as, or combined to form, a heterogeneous suspension. Spectral properties may include one or more non-overlapping dyes, diameter, refractive index, reflectivity, fluorescence intensity, light scatter, Raman spectra, etc.

Modern flow cytometry and microscopy systems typically have more than one fluorescence detector. In some embodiments, a plurality of sets of microbead populations may be used to calibrate multiple detectors or detection channels on an instrument. In some embodiments, a plurality of sets of microbeads, suitable for the calibration of multiple detectors, and distinguishable by spectral properties, may be provided as, or combined to form, a heterogeneous suspension.

For the purpose of calculating MESF, a population of surface-dyed beads may be used which contains the same fluorescent dye that is conjugated to the detection reagent, and which is measured on the same instrument.

For the purpose of assessing the linearity and slope of a detector, it is not necessary to measure the same fluorescent dye as that which was conjugated to the detection reagent, providing both dyes can be measured using the same detector. In some embodiments, a population of internally-labeled microbeads may contain a different fluorescent dye from a population of surface-labeled microbeads designed for calibration of the same detector.

Some fluorescent dyes have very broad excitation and emission spectra. Therefore, for the purpose of assessing the linearity and slope of a detector, it may be possible to use microbeads containing different amounts of the same fluorescent dye to calibrate multiple detectors representing different regions of the light spectrum. In some embodiments, the number of dye molecules internally bound to each microbead may be between 50, 100, 200, 500, 1000, 2000, 5000 molecules and 10,000, 20,000, 30,000, or 50,000 molecules. In some embodiments, the number of dye molecules internally bound to each microbead may be between 100 and 50,000 and in some embodiments the number may be between 1,000 and 30,000. In some embodiments, a series of populations of internally-labeled microbeads may be measured using a plurality of detectors. In some embodiments, any given population of internally-labeled microbeads may be measured using between 1, 2, 3, and 4 detectors and 10, 12, 14, 18, 24, 36, or 48 detectors. Using current, state-of-the-art flow cytometers, the greatest number of fluorescence detectors ever reported in simultaneous use is 17 (see Perfetto et al. Seventeen-colour flow cytometry: unravelling the immune system. Nat Rev Immunol 2004; 4:648-655). As flow cytometry technology advances, the number of available fluorescence detectors may increase, and it should be understood that the methods and kit described in the present invention may be expanded to accommodate any number of fluorescence detectors.

In some embodiments, a computer program may automatically identify multiplexed microbead populations within a heterogeneous suspension. The number of multiplexed microbead populations may be between 2, 3, 5, 10, 20, 40 populations and 100, 200, 300, 400 or 500 populations. In some embodiments, a computer program may automatically calculate a regression equation for each calibrated fluorescent detector.

Instrument performance may vary over time, even within the span of measuring a single experiment. For example, on a flow cytometer, fluctuations in the pressure of the fluidics system (e.g. from bubbles, pump malfunctions, or kinks in tubing) may disrupt the timing with which particles pass through the lasers, resulting in suboptimal measurements. Consequently, an objective of the present invention is to provide a time-stamped indicator of instrument performance, which is measured simultaneously with the experimental sample. In some embodiments, one or more populations of internally-dyed microbeads, which are spectrally distinct from the experimental sample, may be mixed with the experimental sample and measured simultaneously as in-well control beads. In some embodiments, one or more populations of in-well control beads detectable by each detector on the instrument may be mixed with the experimental sample. It is desirable that each population of in-well control beads be spectrally distinguishable, and that the performance of each detector may be monitored simultaneously, with at least one control bead population having a median fluorescence intensity within the linear range of each detector. In some embodiments, the number of in-well control populations may be between 1, 2, and 3 populations and 10, 14, 18, 24, 48, 96, or 128 populations.

Analysis and Calibration

Advances in flow cytometry have enabled the individual cell enumeration of seventeen simultaneous colors (Perfetto et al., Nature Reviews Immunology, 4:648-655 (2004)) and are moving towards the study of genomic and proteomic data subsets (Krutzik and Nolan, 2003; Perez and Nolan, 2002). Methods for the analysis of multiple parameters are well known in the art. See U.S. Ser. No. 61/079,579 for gating analysis.

In some embodiments where flow cytometry is used, flow cytometry experiments are performed and the results are expressed as fold changes using graphical tools and analyses, including, but not limited to a heat map or a histogram to facilitate evaluation. One common way of comparing changes in a set of flow cytometry samples is to overlay histograms of one parameter on the same plot. Flow cytometry experiments ideally include a reference sample against which experimental samples are compared. Reference samples can include normal and/or cells associated with a condition (e.g. tumor cells). See also U.S. Ser. No. 61/079,537 for visualization tools. See also, U.S. Ser. No. 61/120,320.

Fluorescence intensity may be measured in counts, peak height, photons, or other arbitrary units. When displayed as a histogram representing the number of particles observed per value of fluorescence intensity, a homogeneous population of fluorescent microbeads typically appears as a Gaussian distribution. The width of the distribution, described by the coefficient of variance (% CV), is primarily influenced by the measurement 'noise' of the instrument and variability in the number of fluorescence molecules per particle within the population. The % CV of a population of internally-labeled microbeads can remain constant over a period months or years, depending on storage conditions. By comparing the observed % CV of a microbead population to a previously-determined intrinsic % CV for that lot of microbeads, machine performance can be monitored. In some embodiments of the present invention, instrument performance may be monitored, either in real-time or after acquisition, by comparing the observed % CV of a microbead population to a reference value.

The fluorescence intensity of a population of particles, collected as single-particle data, can be summarized into a single numerical value by calculating the mean, median, geometric mean, etc. Median fluorescence intensity (MFI) is a preferred statistic, as it is less influenced by extreme outliers than mean fluorescence intensity. See U.S. Ser. No. 61/120,320. When measuring particles with intrinsic autofluorescence, including polymer microbeads, cells, and nanoparticles, one may measure the MFI of an unlabeled or "blank" population to determine the background-substracted MFI of a labeled population. By "background-subtracted MFI" as used herein is meant the observed MFI of a population of fluorescent-labeled particles, minus the MFI of a population of unlabeled particles constructed of the same material. By measuring at least two microbead populations within the linear range an instrument, and comparing the background-subtracted MFI of each population to previously-determined ERF values, one may determine the slope of the linear range of a fluorescence detector. For example, if a fictional Population X has a background-subtracted MFI of 5,000 and an ERF of 1,000, while a fictional Population Y has a background-subtracted MFI of 25,000 and an ERF of 2,000, the slope of the detector may be calculated by linear regression on a plot of ERF vs. MFI, so in this example the slope is equal to: $[(2000-1000)/(25000-5000)]=0.05$ ERF per unit background-subtracted MFI. By measuring at least one surface-labeled microbead population within the linear range of the same instrument, then using the observed background-subtracted MFI and the slope of the detector to determine the ERF of the population, and comparing the ERF of the population to a previously-determined MESF value, one may calibrate the detector in terms of MESF, a traceable unit of measure. For example, if a fictional Population Z has a background-subtracted MFI of 5,000 and a MESF of 100,000, and the slope of the detector is calculated to be 0.05 ERF per unit of background-subtracted MFI, then Population Z is equivalent to an ERF of 250, and the slope of the detector is equal to: [(100,000 MESF/250 ERF)×0.05]=20 MESF per unit of background-subtracted MFI. In the non-limiting example above, a fictional instrument was calibrated to a traceable unit of measure (MESF) using only four microbead populations. In some embodiments of the present invention, an instrument may be calibrated in terms of MESF by the steps comprising: Plotting the median fluorescence intensity (MFI) of the microbead populations containing internally-bound dyes versus the separately calculated mean ERF of each population, performing a linear regression analysis of said points, and determining the slope of the regression line; determining the MFI of a microbead population containing surface-bound fluorophores of the same species used to label the detection reagent, identifying the point at which said MFI intercepts said regression line, calculating the y-intercept, and rewriting the regression equation in terms of MFI versus MESF.

MESF is a traceable unit, but it has limitations. Fluorescently-labeled detection reagents (e.g. monoclonal antibody) exhibit lot-to-lot variation in terms of the number of fluorophores conjugated per molecule. Consequently, data collected in terms of MESF can be reliably compared between samples stained with a single lot of detection reagent, but not between lots. To obtain data that transcends lot-to-lot labeling variability, it may be desirable to calculate the number of molecules of detection reagent bound per particle, referred to herein as "molecules of detected analyte" (MDA). By determining the MESF per molecule of detection reagent as described above, and obtaining fluorescence data on an instrument calibrated in terms of MESF, MDA may be readily calculated by dividing the observed MESF of a particle or population by the mean MESF per molecule of detection reagent. For example, if a fictional experimental sample Q was stained with a monoclonal antibody with a fictional MESF per molecule of antibody of 6.0, and the Population Q is observed to have a median MESF of 150,000, then the median molecules of detected analyte (MDA) on Population Q is 25,000. MDA is a useful value because it is only influenced by the binding kinetics of the detection reagent, and is independent of the degree of fluorescent labeling, the choice of fluorescent dye, the type of experimental sample, or the instrument. Therefore, data expressed in terms of MDA can be reliably compared between lots, laboratories, instruments, and experiments as long as the same detection reagent is used. In some embodiments of the present invention, an instrument may be calibrated in terms of molecules of detected analyte (MDA) by using the previously-determined mean MESF per molecule of detection reagent, and the previously-determined regression equation for the detector rewritten in terms of MFI versus MESF, to calculate a modified regression equation written in terms of MFI versus molecules of detection reagent.

In some embodiments, a computer program may automatically identify an in-well control bead population that is spectrally distinct from the experimental sample. In some embodiments, a human operator or a computer program may determine a baseline of acceptable instrument performance by measuring the population of in-well control beads when the instrument is known to be performing optimally. In some embodiments, a computer program may monitor instrument performance in real-time using said in-well control beads. In some embodiments, a human operator or computer program may detect hardware failure when the median fluorescence intensity of a population of in-well control beads deviates from baseline measurements by a percentage above an acceptable variation range of between 0.1%, 0.5%, 1%, 2%, 5% and 10%, 15%, or 20% variation. In some embodiments, a computer program may alert the user of suboptimal performance, or pause the analysis based on user-definable settings. In some embodiments, a computer program or human operator may use time-stamped data from in-well control beads to flag or exclude data that were acquired during a time period when the instrument was performing outside a user-specifiable performance range.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entireties.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Other Embodiments

The invention has been described with reference to specific embodiments. Other embodiments will be apparent to those of skill in the art.

Although the present invention has been described in terms of various specific embodiments, it is not intended that the invention be limited to these embodiments. Modification within the spirit of the invention will be apparent to those skilled in the art. In addition, various different actions can be used to affect the data analysis, visualization and/or display described herein.

Those skilled in the art will readily appreciate that many modifications are possible in the exemplary embodiments without materially departing from the novel teachings and advantages of this invention. Accordingly, all such modifications are intended to be included within the scope of this invention as defined in the claims.

EXAMPLES

Example I

Composition of a Kit for Calibrating Three Fluorescent Dyes on a Single-Laser, Three-Color Flow Cytometer In this example, a calibration kit is assembled with microbead populations to calibrate all detectors of a three-color flow cytometer. A Becton-Dickinson FACScan™ flow cytometer is fitted with a 488 nm, air-cooled argon-ion laser, appropriate optics to acquire forward scatter (FSC) and side-scatter (SSC) detectors, as well as appropriate filters and mirrors to direct different bands of the emitted light spectrum (>488 nm) to three fluorescence detectors: FL1 (530/30 nm band), FL2 (585/42 nm band), FL3 (670 nm long-pass). Three fluorescent dyes, FITC (fluorescein-5-isothiocyanate), PE (R-phycoerythrin), and PerCP (peridinin-chlorophyll protein complex) are to be calibrated with the kit on the detectors FL1, FL2 and FL3, respectively. All of these dyes are efficiently excited by the 488 nm laser, but have different emission spectra.

Components of the kit: A plurality of spectrally distinct microbead populations are selected for the purposes of assessing the linearity of the three detectors, and calibrating the detectors in terms of MESF. Eight different 6 μm-diameter polystyrene microbead populations are manufactured with different amounts of fluorescent dyes according to the specifications below. All of the microbead populations have high side scatter and low forward scatter to make them easily distinguishable from human cells. Each population is spectrally distinct in the multidimensional space of FL1, FL2, and FL3 fluorescence intensities. Although beads may exhibit fluorescence on more than one channel, usually due to autofluorescence or spectral overlap, each bead in this example contains only one fluorescent dye. Beads are manufactured with high uniformity, such that fluorescence intensities have a % CV of <5. Example median fluorescence intensities (MFI) on each detector are detailed in the list below for the purpose of illustrating the spectral profile of each microbead population, and are summarized here using the following format: [FL1-H MFI|FL2-H MFI|FL3-H MFI]. Autofluorescence and spectral overlap are not subtracted in the raw MFI measurements listed below.

The eight different populations are:
Population 1: Unlabeled [5|5|5]
Population 2: Low internally-bound FITC, for ERF [50|17.5|5]
Population 3: High internally-bound FITC, for ERF [5,000|1,255|5]
Population 4: Low internally-bound PerCP, for ERF [5|5|50]
Population 5: High internally-bound PerCP, for ERF [5|5|5,000]
Population 6: Intermediate quantity of surface-bound FITC, for MESF [500|130|5]
Population 7: Intermediate quantity of surface-bound PE, for MESF [8|500|5]
Population 8: Intermediate quantity of surface-bound PerCP, for MESF [5|5|500]

There are no populations with internally-bound PE in this kit because they are not needed to calibrate the detectors described in this example. One may determine the slope and linearity of a detector using microbeads labeled with any internally-bound dye, as long as at least two microbead populations, labeled with the same dye, are detectable on the linear range of the detector at a level above background autofluorescence. Using the flow cytometer described in this example, approximately 47.4% of the photons emitted by FITC enter the FL1 detector, and approximately 12.5% enter the FL2 detector. Using the microbeads described in this example, both of the internally-bound FITC microbead populations were detectable on the linear portion of the FL2 detector, at a level above background autofluorescence. Therefore, in this example, the slope and linearity of both the FL1 and FL2 detectors may be accurately determined using the FITC-labeled microbeads.

Determination of ERF and MESF: A reference solution of fluorescein (NIST SRM 1932) is diluted serially to create a series of standard solutions with known concentrations. The standard solutions are measured on a Cary Eclipse fluorescence spectrophotometer (Varian Optical Spectroscopy Instruments, Mulgrave, Australia) fitted with a red-sensitive PMT, using an excitation wavelength of 470 nm and integrating over an emission band from 480 nm to 700 nm. A standard curve is then constructed, from which a regression equation is determined. A suspension of unlabeled microbeads (Population 1) of known concentration is measured using the same fluorescence spectrophotometer and settings to determine the autofluorescence of the unlabeled microbead core. Suspensions of microbead Populations 2, 3, and 6, are then diluted to the same concentration as the unlabeled microbead suspension measured earlier. Using the same fluorescence spectrophotometer and settings, these diluted suspensions of Populations 2, 3, and 6 are measured. The fluorescence intensity of the unlabeled microbead population is subtracted from the values obtained for Populations 2, 3, and 6, to give the background-subtracted fluorescence. The background-subtracted fluorescence values are then compared to the standard curve created earlier, and the mean equivalent number of reference fluorophores (ERF) for each population is determined using the linear regression equation described above, corrected for the fraction of the emission wavelength that is integrated by the fluorescence spectrophotometer, as described in Wang et al., Cytometry Part A, 73A: 279-288, 2008. In this example, since the entire emission spectrum of each fluorophore is integrated by the fluorescence spectrophotometer, the correction factor is negligible. Since Population 6 contains only surface-bound fluorophores, the ERF value of the solution is also the MESF value. The concentration of microbeads in each solution is then determined using a hemocytometer, and this value is used to calculate the ERF or MESF per microbead, for each microbead population. The aforementioned steps are repeated using an emission band from 650 nm to 800 nm and a reference solution of PerCP (PhycoPro™ PerCP, ProZyme, Inc., San Leandro, Calif.) to calculate the ERF or MESF per microbead for Populations 4, 5 and 8. Likewise, the aforementioned steps are repeated using an emission band from 525 nm to 700 nm and a reference solution of PE (PhycoPro™ R-Phycoerythrin, ProZyme, Inc., San Leandro, Calif.) to calculate the ERF or MESF per microbead for Populations 2, 3 and 7. The ERF and MESF per microbead values are provided to the end user for each lot of each microbead population in the kit.

Example II

Method of Calibrating a Single Laser, Three-Color Flow Cytometer in Terms of MESF In this example, a microbead calibration kit is provided as described in Example I, above. Furthermore, a single laser, three-color flow cytometer is conFIGUREd as described in Example I, above. The eight spectrally distinct microbead populations are combined in a suspension in equal proportions, and measured on the cytometer. A listmode FCS data file is imported into FlowJo analysis software (TreeStar Inc., Ashland, Oreg.) and gated to allow separate analysis of each microbead population. The ERF or MESF value of each microbead population is determined by the manufacturer and provided with the kit.

Measurement of the Calibration Microbeads:
The raw observed MFI ([FL1|FL2|FL3]) of each microbead population in the kit is:
Population 1: [5|5|5]
Population 2: [50|17.5|5]
Population 3: [5,000|1,255|5]
Population 4: [5|5|50]
Population 5: [5|5|5,000]
Population 6: [500|130|5]

Population 7: [8|500|5]
Population 8: [5|5|500]

Correction for Autofluorescence and Background:

The unlabeled microbeads (Population 1) had an MFI of 5 on each detector. Therefore, the background-subtracted MFI for each microbead population in the kit, on each detector, is equal to: [raw MFI]−5.

The background-subtracted MFI ([FL1|FL2|FL3]) of each microbead population in the kit is:
Population 1: [0|0|0]
Population 2: [45|12.5|0]
Population 3: [4,995|1,250|0]
Population 4: [0|0|45]
Population 5: [0|0|4,995]
Population 6: [495|125|0]
Population 7: [3|495|0]
Population 8: [0|0|495]

Calculation of MESF Calibration Equations:

The provided ERF values for the internally-bound FITC microbeads (Populations 2 and 3) are plotted versus the background-corrected FL1 MFI of each population, and a linear regression equation is calculated. In this example, the fluorescein ERF (EFF) values of Populations 2 and 3 are 255 and 13760, respectively. Therefore, the linear regression equation is calculated by the least-squares method to be: $y=132.04+2.73x$. In this example, the fluorescein MESF (MEFL) of the surface-bound FITC microbeads (Population 6) is 1186. The linear regression equation and the FL1 MFI of Population 6 are used to interpolate the EFF value: $132.04+2.73(495)=1483$. Dividing the known MEFL value by the interpolated ERF value yields the calibration coefficient, which is used to convert EFF to MEFL for FL1: $1186/1483=0.80$. Using this calibration coefficient and the regression equation above, any FL1 measurement in the linear range of the cytometer may be converted from MFI to EFF and then from EFF to MEFL. To simplify even further, a calibration equation is written that directly converts any FL1 MFI value (x) directly to MEFL (y), by multiplying the slope and the y-intercept of the regression equation by the calibration coefficient: $y=132.04(0.80)+2.73(0.80)x$. Using this same logic and the observed FL2 MFIs from Populations 2, 3 and 7, a calibration equation is calculated expressing FL2 MFI in terms of PE MESF. Finally, using this same logic and the observed FL3 MFIs from Populations 4, 5 and 8, a calibration equation is calculated expressing FL3 MFI in terms of PerCP MESF.

Example III

Method of Monitoring Flow Cytometer Performance Using in-Well Beads

In this example, a microbead calibration kit is provided as described in Example I, above. Furthermore, a single laser, three-color flow cytometer is conFIGUREd as described in Example I, above.

Preparation of the Experimental Sample:

A suspension of 1×106 Ficoll-purified human peripheral blood mononuclear cells (PBMCs) is prepared at $1\times10^6$ cells/mL, and fixed with 1.5% paraformaldehyde for 10 minutes at 21° C. The suspension is centrifuged at 500×g for 5 minutes, and the supernatant is decanted. The resulting cell pellet is resuspended in 100 μL of phosphate-buffered saline.

Addition of in-Well Control Beads:

Suspensions of the internally-labeled microbead Populations 3 and 5 (High FITC and High PerCP, respectively) are each diluted to a concentration of $1\times10^3$ beads/μL with PBS. Then, 10 μL of each bead suspension is added to the PBMC suspension, resulting in a heterogeneous suspension of approximately $10^6$ cells, $10^3$ High FITC beads, and $10^3$ High PerCP beads.

Measurement of the Heterogenous Suspension of Cells and Microbeads:

The heterogeneous suspension is measured on the cytometer, and the forward scatter (FSC) and side scatter (SSC) voltages are adjusted to allow simultaneous visualization of PBMC and microbead events on-scale. Approximately 100,000 events are collected in a time-stamped, listmode FCS data file during a collection period of 40 seconds.

Gating the Microbead Events:

The listmode FCS data file is imported into FlowJo analysis software (TreeStar Inc., Ashland, Oreg.) and the microbead events are initially gated (gate R1) based on low forward scatter ($FSC^{low}$) and high side scatter ($SSC^{high}$) to distinguish them the PBMC events. Next, the microbead events within gate R1 are examined in a biaxial display of FITC versus PerCP fluorescence intensity. Next, the FL1 (FITC)-negative events are gated (gate R2), to restrict the analysis to the PerCP-labeled beads (Population 5). The FL3 fluorescence intensity of each event is then plotted versus the time of collection. The same steps are repeated with the PerCP-negative events within gate R1 (gate R3), to determine the FL1 and FL2 performance over time using the FITC-labeled beads.

Analysis of Time-Stamped Data to Determine Instrument Performance Over Time:

In this example, the operator has determined that the mean and standard deviation of each fluorescence parameter (FL1, FL2 and FL3), when measured over a sliding window of 200 events, should deviate by no more than 50% from the benchmark values obtained during nominal instrument performance. The operator exports the gated events from each bead population as a listmode file and uses a sliding-window algorithm to analyze the data. The operator discovers that the mean FL1 fluorescence dropped by 400% during the last 15 seconds of data collection, suggesting a hardware problem with the FL1 detector arose after 25 seconds of run time. When analyzing the PBMC events in FlowJo, the operator excludes all events acquired after 25 seconds of run time, to eliminate the influence of the hardware defect on the data.

Example IV

Method of Verifying MESF Calibration Using Mass Cytometry and Fluorescent Flow Cytometry In this example, a dual-labeled fluorescent detection reagent is measured by a second method to verify the MESF calibration of an instrument. Because the same sample and detection reagent are measured using different detection methods, this method of comparison controls for any variations in reagent quality or sample preparation. Furthermore, elemental mass spectrometry is an extremely precise method of measuring atomic abundance, so it serves as a highly reliable benchmark for verifying fluorescence-based measurements of molecules of detected analyte (MDA).

A mass cytometer is conFIGUREd to measure single-cell events and isotopic masses greater than 100 AMU. Suitable mass cytometers are manufactured by DVS Sciences (Toronto, ON, Canada) under the CyTOF™ brand. Furthermore, a single laser, three-color flow cytometer is conFIGUREd as described in Example I, above, and calibrated in terms of MESF as described in Example II, above. The mass cytometer uses elemental mass spectrometry to measure isotope tags (i.e. rare earth elements) conjugated to cells or antibodies. An advantage of using a mass cytometer in this context is its ability to quantify the number of atoms of each isotope that are detected. The number of detected atoms may be used to determine the exact number of molecules of an antibody that are bound to a cell, and this value may be compared with the MESF and MDA values determined by fluorescence.

Preparation of a Metal-Tagged Fluorescent Detection Reagent:

A FITC-labeled anti-human CD4 antibody is purchased from Becton-Dickinson. SATP(N-Succinimidyl-5-acetylthiopropionate, Pierce Chemical Company, Rockford, Ill. 61105 USA) is provided and used to add between 3 and 4 sulfhydryl groups per antibody molecule, following the methods described in Duncan, R. J. S., et al., (1983) *Anal. Biochem.*, 132:68-73. A maleimide-functionalized polymer with a mean of 30 DTPA monomers per molecule is provided (MAXPAR™, DVS Sciences, Toronto, ON, Canada) and reacted with the hydroxylamine-treated, labile sulfhydryl groups on the SATP-treated antibody, following the methods described in the MAXPAR™ manufacturer's protocol. The preparation of DTBP-conjugated antibody is resuspended in a solution of 20 mM ammonium acetate, pH 6.0, containing 2.5 mM $^{151}$Europium(III) chloride for 30 minutes. The metal-labeled antibody preparation is purified by centrifuging several times through a Microcon 100 kDa membrane filter column (Millipore, Billerica, Mass.).

Determination of MESF-Per-Molecule of Detection Reagent:

A reference solution of fluorescein (NIST SRM 1932) is diluted serially to create a series of standard solutions with known concentrations. The standard solutions are measured on a Cary Eclipse fluorescence spectrophotometer (Varian Optical Spectroscopy Instruments, Mulgrave, Australia), using an excitation wavelength of 470 nm and integrating over an emission band from 480 nm to 700 nm. A standard curve is then constructed, from which a regression equation is determined. A solution of unlabeled immunoglobulin at the same concentration as the dual metal- and FITC-labeled CD4 antibody preparation is measured using the same fluorescence spectrophotometer and settings to determine the autofluorescence of the unlabeled microbead core. Using the same fluorescence spectrophotometer and settings, the dual metal- and FITC-labeled CD4 antibody preparation is measured. The fluorescence intensity of the unlabeled immunoglobulin preparation is subtracted from the values obtained for the dual metal- and FITC-labeled CD4 antibody preparation, to give the background-subtracted fluorescence. The background-subtracted fluorescence values are then compared to the standard curve created earlier, and the mean molecules of equivalent soluble fluorophores (MESF) for the preparation is determined using the linear regression equation described above, corrected for the fraction of the emission wavelength that is integrated by the fluorescence spectrophotometer, as described in Wang et al., Cytometry Part A, 73A: 279-288, 2008. In this example, since the entire emission spectrum of the fluorophore is integrated by the fluorescence spectrophotometer, the correction factor is negligible.

The dual-labeled antibody preparation is resuspended in phosphate buffered saline (PBS) and is measured using an absorbance spectrophotometer. The absorbance at 280 nm and an appropriate extinction coefficient are used to estimate the concentration of antibody in the solution. This value is used to calculate the MESF per molecule of antibody.

Determination of Metal Atoms-Per-Molecule of Detection Reagent:

An Elan® DRC II plate-based inductively coupled plasma mass spectrometer (ICP-MS) (PerkinElmer, Boston, Mass.) is used to measure the molar concentration of $^{151}$Europium in an aliquot of the dual-labeled antibody preparation. This value is used in combination with the previously determined protein concentration to determine the mean number of metal atoms per molecule of detection reagent.

Staining Cells:

A suspension of $1\times10^6$ Ficoll-purified human peripheral blood mononuclear cells (PBMCs) is prepared at $1\times10^6$ cells/mL, and fixed with 1.5% paraformaldehyde for 10 minutes at 21° C. The suspension is centrifuged at 500×g for 5 minutes, and the supernatant is decanted. The resulting cell pellet is resuspended in 50 µL of phosphate-buffered saline with 0.05% bovine serum albumin (BSA). An aliquot of the dual-labeled antibody preparation is diluted to 1000 ng/mL in PBS with 0.05% bovine serum albumin (BSA). An equal volume (50 µL) of the 1000 ng/mL solution is added to the cell suspension for staining. The mixture is vortexed, then incubated at room temperature, rotating at 200 RPM in the dark, for 30 minutes. The cells are washed by adding 2 mL PBS with 0.05% bovine serum albumin (BSA), centrifuging to form a pellet, and aspirating the supernatant. Washing is repeated two additional times. The cell pellet is resuspended in a solution of 500 mM rhodium(III)-conjugated DNA intercalator (9,10-phenanthrenequinone diimine:rhodium(III)), as described in Ornatsky et al., Anal Chem (2008) vol. 80 (7) pp. 2539-47. The mixture is incubated 15 minutes at room temperature. Washing is repeated four additional times.

Comparison of Molecules Detected Analyte (MDA) Values Determined by Flow Cytometry and CyTOF:

The suspension of stained cells is split evenly across two tubes. The first tube is measured using the FACScan™ flow cytometer, and fluorescence data is collected using the FL1 detector, then converted to MESF as described in Example II. Using this value and the previously determined MESF-per-molecule of detection reagent, the number of molecules of detected analyte (MDA) per cell is determined.

The second tube is measured using the CyTOF mass cytometer to collect $^{151}$Eu data, which is integrated for each cellular event, as detected by the pulse of rhodium atoms reaching the detector. Standard europium chloride solutions are used to calculate the ionization efficiency of the CyTOF and the percentage of ions that reach the detector. This value is used to extrapolate the number of $^{151}$Eu atoms per cell. Using this value and the previously determined metal atoms-per-molecule of detection reagent, the number of molecules of detected analyte (MDA) per cell is determined.

The FACScan and CyTOF MDA values are compared to verify the precision of the MESF calibration, and troubleshoot as needed.

What is claimed is:

1. A calibration kit comprising:
   a. a set of populations of microbeads, the microbeads having a surface and being made of a particular material;
   b. each of said microbead populations having a median fluorescence intensity within a linear detection range of a fluorescence detector to be calibrated;
   c. each of said microbead populations having spectral properties that are sufficiently different from any other microbead populations in the same set to allow discrimination thereof;
   d. at least two microbead populations of said set containing a different and determinable quantity of one or more non-overlapping internally-bound fluorophores measurable by a fluorescence detector to be calibrated;
   e. at least one microbead population of said set, having bound to the surface of each microbead, either directly or indirectly, a determinable quantity of one or more non-overlapping fluorophores measurable by a fluorescence detector to be calibrated; and
   f. at least one unlabeled microbead population of said set, to serve as a control for autofluorescence of said material.

2. A microbead calibration kit according to claim 1, wherein said at least two populations comprise microbeads formed by polymerization and containing a uniform distribution of fluorophore throughout the polymer.

3. A microbead calibration kit according to claim 1, wherein said at least two populations of microbeads with internally-bound fluorophores are provided in a single liquid suspension.

4. A microbead calibration kit according to claim 1, wherein the microbead populations are provided in a single liquid suspension.

5. A microbead calibration kit according to claim 1, wherein at least one microbead population contains a determinable quantity of one or more non-overlapping internally-bound fluorophore measurable by a fluorescence detector to be calibrated, and has spectral properties that are sufficiently different from an experimental sample to allow reliable discrimination thereof, and is provided in a separate suspension to allow mixing with the experimental sample as an internal control.

6. A microbead calibration kit according to claim 1, wherein said microbeads have a diameter in the range of from about 0.5 to about 70 microns.

7. A microbead calibration kit according to claim 1, wherein each of said microbeads is comprised of a polymeric seed particle and one or more monomeric swelling agents.

8. A microbead calibration kit according to claim 1, wherein said microbeads have a refractive index in the range of from about 1.2 to about 1.8.

9. A microbead calibration kit according to claim 1, wherein said spectral properties are selected from the group consisting of: one or more non-overlapping dyes, diameter, refractive index, reflectivity, fluorescence intensity, light scatter, and Raman spectrum.

10. A method for calibrating a flow cytometer or fluorescence microscope in terms of molecules equivalent soluable fluorescence (MESF), comprising the steps of:
  a. providing a microbead calibration kit as described in claim 1;
  b. contacting an experimental sample with a detection reagent containing a fluorophore to be calibrated, said fluorophore being the same as the surface-bound fluorophores in the kit;
  c. measuring the at least one unlabeled microbead population with the flow cytometer or fluorescence microscope to be calibrated to obtain a value and subtracting this value from a value obtained when the experimental sample is measured with the flow cytometer or fluorescence microscope to correct for autofluorescence of the microbeads;
  d. comparing each microbead population by solution fluorimetry to reference solutions of fluorophores to determine a mean equivalent number of reference fluorophores (ERF) or a mean MESF of each population;
  e. comparing the detection reagent by solution fluorimetry to reference solutions of the same fluorophore contained in the detection reagent, to determine the mean MESF per molecule of detection reagent;
  f. measuring the microbead populations in the kit with the flow cytometer or fluorescence microscope to be calibrated;
  g. plotting a median fluorescence intensity (MFI) of the microbead populations containing one or more non-overlapping internally-bound fluorophores versus a reference solution of a fluorophore to determine the MESF of each population, performing a linear regression analysis of said plot using a regression equation to form a linear regression line, and determining a slope of the regression line;
  h. determining the MFI of a microbead population containing the surface-bound fluorophores, and identifying a point at which said MFI intercepts said regression line, calculating a y-intercept, and rewriting the regression equation in terms of MFI versus MESF for the fluorophores used in step (d);
  i. using said mean MESF per molecule of detection reagent to calculate a modified regression equation written in terms of MFI obtained in step (h) versus molecules of detection reagent; and
  j. using said modified regression equation to determine the number of molecules of said detection reagent bound to said experimental sample to form a value called molecules of detected analyte (MDA).

11. The method of claim 10, wherein said detection reagent is selected from the group consisting of antibodies, peptides, nucleic acids, viability dyes, intercalating agents, lipid dyes, and carbohydrate polymers.

12. The method of claim 10, wherein a computer program automatically identifies multiple microbead populations and calculates a regression equation for the calibrated fluorophore.

13. The method of claim 10, further comprising mixing at least one microbead population in a well with the experimental sample prior to data collection.

14. The method of claim 10, further comprising mixing one or more populations of microbeads with the experimental sample and measuring fluorescence intensity.

15. The method of claim 10, further comprising mixing one or more populations of microbeads with the experimental sample and recording a time that data is collected.

16. The method of claim 10, wherein performance or data quality is monitored in real-time by monitoring fluorescence intensity of one or more microbead populations mixed with the experimental sample, and comparing said fluorescence intensity to an acceptable target range.

17. The method of claim 10, further comprising recording a time that fluorescence intensity data is collected and comparing the fluorescence intensity data to an acceptable target range.

18. The method for calibrating a flow cytometer or fluorescence microscope according to claim 10, wherein said at least two populations of microbeads containing internally-bound fluorophores are compared by solution fluorimetry to reference solutions of fluorophore to determine the equivalent number of reference fluorophores (ERF) of said populations.

19. The method for calibrating a flow cytometer or fluorescence microscope according to claim 10, wherein said at least two populations of microbeads containing internally-bound fluorophores are measured by flow cytometry to determine the intrinsic coefficient of variance of said populations, prior to the calibration of the flow cytometer or fluorescence microscope.

20. The method for calibrating a flow cytometer or fluorescence microscope according to claim 10, wherein more than one population of microbeads containing surface-bound fluorophores are provided as separate liquid suspensions, and are mixed immediately prior to measurement.

21. The method for calibrating a flow cytometer or fluorescence microscope according to claim 10, wherein each microbead population recited in step d is compared by solution fluorimetry to reference solutions of a fluorophore to determine the median molecules equivalent soluble fluorescence (MESF) or the equivalent number of reference fluorophores (ERF) of each population.

* * * * *